(12) United States Patent
Copperman et al.

(10) Patent No.: US 7,592,146 B2
(45) Date of Patent: Sep. 22, 2009

(54) PROTOCOL FOR DETECTING PROTEINS IN A CULTURE CONTAINING AN EMBRYO

(76) Inventors: Alan Copperman, 399 E. 72nd St., Apt. 16A, New York, NY (US) 10021; Lawrence Grunfeld, 22 Jerome Ave., New Rochelle, NY (US) 10804; Tanmoy Mukherjee, 66 Highland Ave., Glen Ridge, NJ (US) 07028; Benjamin Sandler, 168 Vaccaro Dr., Cresskill, NJ (US) 07626

( * ) Notice: Subject to any disclaimer, the term of this patent is extended or adjusted under 35 U.S.C. 154(b) by 2 days.

(21) Appl. No.: 11/565,317

(22) Filed: Nov. 30, 2006

(65) Prior Publication Data

US 2008/0124711 A1 May 29, 2008

Related U.S. Application Data

(60) Provisional application No. 60/748,263, filed on Dec. 6, 2005.

(51) Int. Cl.
*G01N 33/00* (2006.01)
*G01N 33/53* (2006.01)

(52) U.S. Cl. .................. 435/7.1; 435/7.21; 436/501; 436/518

(58) Field of Classification Search ........................ None
See application file for complete search history.

(56) References Cited

U.S. PATENT DOCUMENTS 4,680,258 A    7/1987  Hammerling et al.
5,648,468 A *  7/1997  Spaulding ................ 530/359

OTHER PUBLICATIONS

Johnson L.A., DTW (Deutsche tierarztiliche Wochenschrift, Aug.-Sep. 1996, vol. 1103., No. 8-9, pp. 288-291—English Abstract only.*
Gardon et al. (Theriogenology, vol. 62, 2004, pp. 35-43).*
Wachtel (Biology of Reproduction, vol. 22, pp. 1-8, 1980).*
Oglivie et al., "Preimplantation Genetic Diagnosis—An Overview", J Histochem Cytochem, 2005; 53: pp. 255-260.
Yanagimachi, "Intracytoplasmic sperm injection experiments using the mouse as a model", Hum Reprod. 1998;13: pp. 87-98.
Armstrong et al., "Advances in production of embryos in vitro from juvenile and prepubertal oocytes from the calf and lamb", Reprod Fertil Dev. 1997,9: pp. 333-339.
Hoshi, "In vitro production of bovine embryos and their application for embryo transfer", Theriogenology, 2003;59: pp. 675-685.
Bavister, "A Consistently Successful Procedure for in Vitro Fertilization of Golden Hamster Eggs", Gamete Research 1989; 23: pp. 139-158.
Niemann, et al., "Progress in Reproductive Biotechnology in Swine", Theriogenology, 2001;56: pp. 1291-1304.
Wilmut, et al., "Viable offspring derived from fetal and adult mammalian cells", Nature, 1997;385: pp. 810-813.
Campbell et al., "Sheep cloned by nuclear transfer from a cultured cell line", Nature, 1996;380 pp. 64-66.
Cibelli, et al., "Cloned Transgenic Calves Produced from Nonquiescent Fetal Fibroblasts", Science, 1998; 280: pp. 1256-1258.
Collas et al., "Influence of Cell Cycle Stage of the Donor Nucleus on Development of Nuclear Transplant Rabbit Embryos", Biology of Reproduction, 1992:46; pp. 492-500.
Baguisi, et al., "Production of goats by somatic cell nuclear transfer", Nature Biotech, 1999; 17: pp. 456-461.
Wakayama et al., "Full-term development of mice from enucleated oocytes injected with cumulus cell nuclei", 1998; 394: pp. 369-374.
Cohen et al., "Laboratory techniques for handling gametes and embryos", British Medical Bulletin 1990; 46: pp. 643-653.
Gandolfi et al., "Stimulation of early embryonic development in the sheep by co-culture with oviduct epithelial cells", J. Reprod. Fert.; 1987; 81: pp. 23-28.
Eyestone, et al., "Co-culture of early cattle embryos to the blastocyst stage with oviducal tissue or in conditioned medium", J. Reprod. Fert., 1989, 85; pp. 715-720.
Von Heijne, "A new method for predicting signal sequence cleavage sites", 1986; 14: pp. 4683-4690.
Boiso, "Fundamentals of human embryonic growth in vitro . . . ", Reprod Biomed Online, 2002; 5: pp. 328-350.
Squires, "The Veterinary Clinics of North America", Vet Clin North Am Equine Pract. 1996; 12: pp. 31-45.
Guichard, et al. " Radioimmunoassay of Steroids Produced by Cultured Chick Embryonic Gonads: Differences according to Age, Sex and Side" General and Comparative Endocrinology 32, 255 265 (1977).
Jimenez, et al. "Hyperglycemia-Induced Apoptosis Affects Sex Ration of Bovine and Murine Preimplantation Embryos" Molecular Reproduction and Development 65: 180-187 (2003).
White, et al. "Expression of a Male-Specific Factor on Various Stages of Preimplantation Bovine Embyros" Biology of Reproduction 37, 867-873 (1987).
Avery, et al. "Sex Determination of Bovine Embryos Using H-Y Antibodies", Acta Vet. Scand. 1989, 30, 155 -164.
Larson, et al. "Sexual dimorphism among bovine embryos in their ability to make the transition to expanded blastocyst and in the expression of the signaling molecule IFN-tau" PNAS, 2001; 98 9677-9682.
Kimura, et al. "Effect of Oxidative Stree and Inhibitors of the Pentose Phosphate Pathway on Sexually Dimorphic Production of IFN-t by Bovine Blastocysts" Molecular Reproduction and Development 68: 88-95 (2004).
Noci, et al. "Embryonic soluble HLA-G as a marker of developmental potential in embryos" Human Reproduction vol. 20, No. 1 pp. 138-146 ( 2005).

* cited by examiner

*Primary Examiner*—Lisa V Cook
(74) *Attorney, Agent, or Firm*—Darby & Darby P.C.

(57) ABSTRACT

The present invention provides methods to determine the sex of an embryo by detecting the presence of a protein associated with the Y chromosome in a sample of culture medium obtained by sampling a culture medium containing the embryo. The present invention further provides methods to identify a protein associated with the Y chromosome as a protein present in a sample of culture medium obtained by sampling a culture medium containing a male embryo, but absent in a sample of culture medium obtained by sampling a culture medium containing a female embryo.

14 Claims, No Drawings

PROTOCOL FOR DETECTING PROTEINS IN A CULTURE CONTAINING AN EMBRYO

This application claims the benefit of U.S. provisional application No. 60/748,263, filed Dec. 6, 2005, the contents of which are hereby incorporated by reference in their entirety.

FIELD OF THE INVENTION

The present invention provides methods to determine the sex of an embryo by detecting the presence of a protein associated with the Y chromosome in a sample of culture medium obtained by sampling a culture medium containing the embryo. The present invention further provides methods to identify a protein associated with the Y chromosome as a protein present in a sample of culture medium obtained by sampling a culture medium containing a male embryo, but absent in a sample of culture medium obtained by sampling a culture medium containing a female embryo.

BACKGROUND OF THE INVENTION

In mammals, the genetic content of a normal cell is made up of pairs of autosomal chromosomes (designated by number) plus two sex chromosomes (designated by the letters "X" and "Y").

The total number of autosomal chromosomes varies slightly from species to species. For example, a normal cell in the human body contains a total of 44 autosomal chromosomes, in the form of pairs of chromosomes 1 through 22. In contrast, a normal cell in a mouse has a total of 38 autosomal chromosomes (in the form of pairs of chromosomes 1 through 19) while a normal cell in a horse has a total of 62 autosomal chromosomes (in the form of pairs of chromosomes 1 through 31).

For all mammals, the total number of sex chromosomes in a normal cell is 2. Normal female mammals have two X chromosomes in each cell, while normal male mammals have one X chromosome and one Y chromosome in each cell.

A variety of techniques are well known in the art for the generation of mammalian embryos in vitro, including in vitro fertilization (IVF) and nuclear transfer. Such techniques are routinely used to generate viable embryos which are transferred to the uterus of a recipient female for gestation and birth. In particular, in vitro fertilization (IVF) is routinely applied in clinical settings to allow otherwise infertile women to become pregnant and carry a baby to term.

For in vitro fertilization (IVF), oocytes retrieved from a female are fertilized using sperm retrieved from a male (for example, by simple mixing of oocyte and sperm or by intracytoplasmic injection of sperm into the oocyte), and embryonic development is initiated in vitro.

For nuclear transfer, the nucleus of a donor cell (e.g., a somatic cell) is transferred into an enucleated oocyte, for example, by cell-fusion between an enucleated oocyte and a nucleus donor cell. Following nuclear transfer the oocyte is activated to stimulate embryonic development. In other nuclear transfer methods, the nucleus of a donor cell (e.g., a somatic cell) is transferred into an enucleated fertilized oocyte, without the need for subsequent activation of the oocyte.

In such method following in vitro generation of the embryo, the developing embryo is maintained in in vitro culture, generally until the 6 or 8 cell stage, and then the embryo is transferred to the uterus of a recipient female for implantation and further development.

Preimplantation genetic diagnosis (PGD) is a technique used to provide genetic information about embryos generated in vitro prior to transfer of the embryo to a recipient female for pregnancy. For example, PGD has been applied to in vitro embryos to identify aneuploidy of autosomal chromosomes and sex chromosomes, to determine the sex of an embryo, and for the diagnosis of a variety of genetic diseases (see, for example, Ogilvie et al. *J Histochem Cytochem* 2005; 53:255-260 and Sermon. *Human Reprod Update* 2002; 8:11-20).

Prior to the development of PGD technology, the sex of a developing embryo could only be determined after the establishment of an in vivo pregnancy. Similarly, genetic diseases and conditions could only be diagnosed after the establishment of pregnancy. Thus, in human clinical settings where a pregnancy contained a child affected with a genetic disease or condition, the couple had to decide between termination of the pregnancy or delivery of an affected child whose quality of life could be severely hindered by the genetic condition.

For PGD, in vitro generated embryos are cultured under carefully controlled conditions until they reach a stage in which six to eight discrete cells are formed. In the case of IVF procedures performed on humans, this stage is usually attained three days following fertilization of the oocyte. On the day of diagnosis, the embryo is positioned by delicate micromanipulators so that a single cell can be extracted (biopsied) and separated from the remaining cells which are left intact. The genetic content of the biopsied blastomere is then assessed, for example, by polymerase chain reaction or by Fluorescence In-Situ Hybridization (FISH). Using these techniques, the number and type of chromosomes present can be determined and the health of the embryo deduced. Where an embryo of a particular sex is desired, such embryos may be identified for consideration for transfer to the recipient female. Similarly, where a genetic abnormality is detected, the particular embryo is removed from consideration for transfer to the recipient female.

For example, for FISH-based PGD of human embryos, probes are currently available to analyze up to 9 different chromosomes including the autosomal chromosomes 13, 15, 16, 17, 18, 21, and 22 and both (X and Y) sex chromosomes. Thus, FISH-based PGD may be used to determine the sex of an embryo prior to transfer. Similarly, FISH-based PGD may be used to diagnose Down's syndrome, a condition in which three copies of chromosome 21 are present.

However, removal of one or more blastomeres from the developing embryo for the purpose of performing PGD can decrease embryo viability, resulting in reduced rates of survival and continued development of embryos prior to implantation, and to reduced rates of viable pregnancy upon transfer to the recipient female. Furthermore, in certain cases, the genetic content of a single blastomere may not be representative of the embryo as a whole (e.g., where the developing embryo is a mosaic, i.e., where the genetic content of all cells is not identical). In such cases, PGD may provide an inaccurate diagnosis. For example, if the biopsied blastomere has a normal chromosomal content, while some or all of the remaining blastomeres have a chromosome abnormality, the embryo could be inaccurately identified as chromosomally normal.

Therefore, a need exists in the art for methods to assess the genetic content of an in vitro embryo, which are non-invasive (i.e., do not damage the embryo) and which accurately reflect the genetic content of the embryo as a whole. In particular, a need exists in the art for non-invasive and accurate methods to determine the sex of an in vitro embryo prior to transfer to a recipient female.

The present invention fulfills this need in the art by providing a simple, non-noninvasive method for determining the genotype of an embryo in vitro, particular for identifying the sex of the embryo, by detection of a protein associated with the genotype in a sample of culture medium obtained from a culture medium containing the embryo. This method is also broadly applicable to the diagnosis of genetic conditions and diseases, by detection of proteins associated with a genetic disease or condition in culture medium containing the embryo. This method may be used to determine the genotype of the embryo prior to implantation without adversely affecting embryo viability.

SUMMARY OF THE INVENTION

The invention is directed to a method to determine a genotype of an embryo, which comprises:
(a) sampling a culture medium containing an embryo; and
(b) detecting the presence of a protein associated with the genotype in the sample of culture medium, wherein the presence or absence of the protein associated with the genotype determines the genotype of the embryo.

In certain embodiments, the embryo is a human embryo. In certain other embodiments, the embryo has a total cell number of from 6 to 8 cells.

The invention as also direct to a method for identifying the sex of an embryo, which comprises:
(a) sampling a culture medium containing an embryo;
(b) detecting the presence of a protein associated with the Y chromosome in the sample of culture medium; and
(c) identifying the sex of the embryo as a male if a protein associated with the Y chromosome in present or as a female if a protein associated with the Y chromosome is not present.

In certain embodiments, the protein associated with the Y chromosome is selected from the group consisting of: TGFβ-induced transcription factor 2-like protein, Protocadherin 11Y, Sex determining region Y protein, Ribosomal protein S4 Y isoform 1, Zinc finger Y chromosomal protein, Amelogenin Y, Transducin (beta) like 1 protein Y, Protein kinase Y, Ubiquitin specific protease 9Y, Dead Box Y protein, Ubiquitous TPR motif Y, Thymosin (beta) 4 Y, Neuroligin 4 isoform Y, Chromosome Y open reading frame 15A, Chromosome Y open reading frame 15B, SMC (mouse) homolog, Translation initiation factor 1AY, Ribosomal protein S4 Y isoform 2, Testis specific protein Y, Variable charge Y, XK related Y protein, Chromodomain Y protein, Heat shock transcription factor protein Y, RNA binding motif Y protein, PTP-BL related Y protein, Deleted in azoospermia (DAZ), novel protein similar to lysozyme C, and mixtures thereof. In other embodiments, the protein associated with the Y chromosome is a Homo sapiens similar to RNA binding motif protein, Y chromosome, family 2 member B (LOC347598) protein.

In certain embodiments, the embryo is a human embryo. In certain embodiments, the embryo has a total cell number of from 6 to 8 cells.

The invention is also directed to a method for identifying a protein associated with the Y chromosome, which comprises:
(a) detecting the presence of at least one protein in a sample of culture medium obtained by sampling a culture medium containing a male embryo;
(b) detecting the presence of at least one protein in a sample of culture medium obtained by sampling a culture medium containing a female embryo; and
(c) identifying a protein associated with the Y chromosome as a protein present in the sample of culture medium of step (a) but absent in the sample of culture medium of step (b).

In certain embodiments, the male embryo and the female embryo are both human embryos. In some embodiments, the male embryo has a total cell number of from 6 to 8 cells and the female embryo has a total cell number of from 6 to 8 cells.

The method is further directed to a method for identifying the sex of an embryo, which comprises:
(a) sampling a culture medium containing an embryo;
(b) detecting the presence of a protein associated with the Y chromosome in the sample of culture medium; and
(c) identifying the sex of the embryo as a male if a protein associated with the Y chromosome in present or as a female if a protein associated with the Y chromosome is not present, wherein the protein associated with the Y chromosome is identified according to the methods of the present invention.

In certain embodiments, the embryo is a human embryo. In certain embodiments, the embryo has a total cell number of from 6 to 8 cells.

DETAILED DESCRIPTION

The present invention provides methods to determine a genotype of an embryo by sampling a culture medium containing the embryo and detecting the presence of a protein associated with the genotype in the culture medium sample, wherein the presence or absence of the protein associated with the genotype determines the genotype of the embryo.

In particular, the present invention provides methods to determine the sex of an embryo, which method comprises the steps of: (a) sampling a culture medium containing an embryo; (b) detecting the presence of a protein associated with the Y chromosome in the sample of culture medium; and (c) identifying the sex of the embryo as a male if a protein associated with the Y chromosome in present or as a female if a protein associated with the Y chromosome is not present.

The embryos to be used in the context of the present invention are mammalian embryos contained in an in vitro culture medium. Such embryos include embryos generated in vitro and embryos generated in vivo.

Embryos

Embryos may be generated in vitro by any of the techniques well known in the art, such as in vitro fertilization (IVF), including IVF performed by simple mixing of oocyte and sperm or by intracytoplasmic injection of sperm into an oocyte, and nuclear transfer.

For in vitro fertilization (IVF), oocytes retrieved from a female are fertilized using sperm retrieved from a male (for example, by simple mixing of oocyte and sperm or by intracytoplasmic injection of sperm into the oocyte), and embryonic development is initiated in vitro. Protocols and methods for IVF are well established in the art for a variety of mammals, including humans (see, for example, Boiso et al. *Reprod Biomed Online*. 2002; 5:328-350; Frydman et al. *Hum Reprod*. 1988; 3:559-561; Tarin and Pellicer. *Ann Acad Med Singapor* 1992; 21:492-497; Kenny. *Br J Obstet Gynaecol*. 1995; 102:317-325; Mansour. *Hum Reprod Update*. 1998; 4:43-56; and Evans et al. *Obstet Gynecol Surv.* 1980; 35:71-81), mice (see, for example, Yanagimachi. *Hum Reprod*. 1998; 13:87-98 and Sato et al. *Horm Res*. 1995; 44 Suppl 2:4-8), sheep (see, for example, Armstrong et al. *Reprod Fertil Dev.* 1997; 9:333-339), cows (see, for example, Hoshi. *Theriogenology*. 2003; 59:675-685 and Marquant-Leguienne and Humblot. *Theriogenology*. 1998; 49:3-11), hamsters (see, for example, Bavister. *Gamete Res.* 1989; 23: 139-158); horses (see, for example, Squires. *Vet Clin North Am Equine*

*Pract.* 1996; 12:31-45 and Hinrichs. *Theriogenology* 1998; 49:13-21) and pigs (see, for example, Niemann and Rath. *Theriogenology.* 2001; 56:1291-1304 and Robl and First. *J Reprod Fertil Suppl.* 1985; 33:101-114).

IVF protocols may be generally summarized as having four stages, as follows:

Stage One: Ovarian Stimulation and Monitoring. In order to maximize the patient's chances for successful fertilization, a patient undergoing IVF takes hormones in the form of injections to increase the number of eggs produced in a given month. Monitoring is performed to continuously follow a woman's ovarian response, allowing the physician to adjust and time medication dosage appropriately.

Stage Two: Ovum Retrieval. With the patient sedated and comfortable, the ova or eggs are retrieved through the vagina under ultrasound guidance.

Stage Three: Culture and Fertilization. The oocytes are fertilized with sperm from the male partner. At times, the sperm are put down on top of the oocyte. In other cases, especially when there are less than one million living sperm, ICSI or intracytoplasmic sperm injection is used catch a single sperm and inject it directly into the oocyte.

Stage Four: Embryo Transfer. Either three or four of the best embryos are transferred directly into the uterus and allowed to implant. The remaining healthy embryos may be cryopreserved (frozen) The pregnancy test is performed 11 days after embryo transfer. In a good program with a high quality laboratory, a woman under the age of 40 should become pregnant approximately 50% of the time For nuclear transfer, the nucleus of a donor cell (e.g., a somatic cell) is transferred into an enucleated oocyte, for example, by cell-fusion between an enucleated oocyte and a nucleus donor cell. Following nuclear transfer the oocyte is activated to stimulate embryonic development. In other nuclear transfer methods, the nucleus of a donor cell (e.g., a somatic cell) is transferred into an enucleated fertilized oocyte, without the need for subsequent activation of the oocyte. Various types of cells can be employed as donors for nuclei to be transferred into oocytes, including adult, fetal or embryonic cells, at various stages of differentiation, ranging from undifferentiated to fully differentiated, in various cell cycle stages, e.g. both quiescent and proliferating cells, and obtained form either somatic or germline tissues. Donor nuclei may be introduced into oocytes by means of fusion, induced electrically or chemically, or by microinjection.

Protocols and methods for nuclear transfer are well established in the art (see, for example Wilmut et al. Nature 1997; 385:810-813; Prather and First. *J. Reprod. Fert.* 1990; Suppl 41:125-134; Cibelli et al. *Science* 1998; 280:1256-8; U.S. Pat. No. 6,600,087; Dominko et al. *Biol. Reprod* 1999; 6:1496-1502; Published PCT application WO 99/37143; Published PCT application WO 98/07841; Published PCT application WO 97/07669; Published PCT application WO 98/30683; Published PCT application WO 98/39416; U.S. Pat. No. 6,147,276; U.S. Pat. No. 6,781,030; U.S. Pat. No. 6,635,802; and U.S. Pat. No. 5,945,577). For example, nuclear transfer protocols are well established in the art for sheep (see, for example, Campbell et al. *Nature* 1996; 380: 64-66 and Liu et al. *Mol Reprod Dev* 1997; 47:255-264), cows (see, for example, Cibelli et al. *Science* 1998; 280:1256-8; Bordignon et al. *Mol Reprod Dev* 1998; 49:29-36; Tanaka et al. *Jpn. J. Vet. Res.* 1995; 43:135-143; Kato et al. *Science* 1998; 282:2095-2098; Wells et al. *Biol. Reprod.* 1999; 60:996-1005; Kubota et al. *Proc. Natl. Acad. Sci. USA* 2000; 97:990-995; and Vignon et al. *Life Sciences* 1998; 321:735-745), rabbits (see, for example, Collas et al. *Biol Reprod* 1992; 46:492-500) goats (see, for example, Baguisi et al. *Nature Biotech* 1999; 17:456-461 and Keefer et al. *Biology of Reproduction* 2001; 64:849-856), pigs (see, for example, U.S. Pat. No. 6,700,037 and Liu et al. *Int. J. Dev. Biol.* 1995; 39:639-644), and mice (see, for example, Wakayama et al. *Nature* 1998; 394:369-374 and Wakayama and Yanagimachi. Nature Genetics 1999; 22:127-128).

Alternatively, embryos generated in vivo may be retrieved from a pregnant mammal (e.g., a female laboratory mouse sacrificed 1.5 days post coitus) and maintained in in vitro culture. Techniques for the mating of mammals (including mice, cows, pigs and goats) and collection of the embryos are well established in the art (see, for example, Murray et al., eds. *Transgenic Animals in Agriculture* Oxford University Press, Hogan et al. *Manipulating the Mouse Embryo 2$^{nd}$ Edition.* Cold Spring Harbor Press, 1994; Jackson and Abbott, eds. *Mouse Genetics and Transgenics: A Practical Approach.* Oxford University Press, 2000; U.S. Pat. No. 5,633,076; U.S. Pat. No. 6,271,436; U.S. Pat. No. 5,907,080).

The embryos thus generated in vitro or in vivo are subsequently cultured in vitro to develop into embryos, which may be implanted in the oviducts of pseudopregnant female animals. Methods for the in vitro culture of mammalian gametes and other mammalian cells, and for the culture of mammalian embryos are well established in the art (see, for example, Cohen et al. *Br Med Bull* 1990; 46:643-653). For example, such methods of protocols are well established for mice (see, for example, Hogan et al. *Manipulating the Mouse Embryo 2$^{nd}$ Edition.* Cold Spring Harbor Press, 1994), rabbits (see, for example, Hammer et al. Nature 1985; 315:680) sheep (see, for example, Hammer et al. *Nature* 1985; 315:680; Gandolfi et al. *J. Reprod. Fert.* 1987; 81:23-28; and Rexroad et al. *J. Anim. Sci.* 1988; 66:947-953), pigs (see, for example, Hammer et al. *Nature* 1985; 315:680); cows (see, for example, Eyestone et al. *J. Reprod. Fert* 1989; 85:715-720 and Goto. *Mol Reprod Devel.* 1993; 36:288-290), and humans (see, for example, Boiso et al. *Reprod Biomed Online.* 2002; 5:328-350; Devreker and Englert. *Eur J Obstet Gynecol Reprod Biol* 2000; 92:51-56; and Gardner and Lane. *Hum Reprod.* 1998; 13:148-159).

In preferred embodiments, the embryo is a human embryo generated in vitro. In preferred embodiments, the embryo is a pre-implantation embryo. In particularly preferred embodiments, the embryo has 6 to 8 cells.

Genotypes

Genotypes to be determined in accordance with the method of the invention include, but are not limited to, total chromosome number (i.e., ploidy), sex (i.e., as defined by the presence of the sex chromosomes), chromosome structure (e.g., the presence or absence of translocations, inversions, duplications and/or deletions), endogenous gene sequence and/or structure (e.g., identification of gene allele and/or of the presence or absence of mutations), and presence of exogenous nucleic acid sequences (e.g., presence of a transgene or retrovirus).

In particular embodiments, the genotype to be determined is the presence or absence of the Y chromosome.

Protein Associated with a Genotype

By the term "protein associated with a genotype" is meant any protein whose presence or absence is correlated with a specific genotype. Such proteins include wildtype endogenous proteins (e.g., a protein encoded on chromosome 1 which is only expressed when chromosome 1 is present or Ornithine Transcarbamylase (OTC) which is not present in X-linked Ornithine Transcarbamylase Deficiency due to mutation of the OTC gene), mutant endogenous proteins (e.g., the BCR-ABL fusion protein of Chronic Myeloid Leukemia formed by a reciprocal translocation between the long arms of chromosomes 9 and 22), and exogenous proteins (e.g., Green Fluorescent Protein encoded by a chromosomally integrated transgene).

In the context of the present invention, it is preferable that the protein associated with a genotype be a secreted protein.

It is within the skill of one of ordinary skill in the art to determine if a protein is a secreted protein. For example, analysis of the amino acid sequence of a protein can be used to determine if the protein contains a signal sequence to direct secretion (see, for example, von Heijne *Nucl. Acid. Res.* 1986; 14:4683-4690; Harcus et al. *Genome Biol* 2004; 5:R39; and Klee and Ellis. *BMC Bioinformatics* 2005; 6:256). In another example, a nucleotide sequence encoding the protein may be cloned, the encoded protein recombinantly expressed in a mammalian host cell, and the extracellular and intracellular distribution of the expressed protein determined. Techniques for the cloning of nucleotide sequences, the recombinant expression of proteins, and the determination of cellular distribution of an expressed protein are well established in the art (see, for example, Glover, ed. *DNA Cloning: A Practical Approach. $2^{nd}$ Edition. Volumes I-IV*. Oxford University Press, 1999; Ausubel et al., eds. *Current Protocols in Molecular Biology*. John Wiley & Sons, Inc., 1994; Dieffenbach and Dveksler, eds. *PCR Primer: A Laboratory Manual. $2^{nd}$ Edition*. Cold Spring Harbor Laboratory Press, 2003; Sambrook et al. *Molecular Cloning: A Laboratory Manual, Third Edition*. Cold Spring Harbor Laboratory Press, 2001; McPherson et al., eds. *PCR: A Practical Approach*. Oxford University Press, 1991; McPherson et al., eds. *PCR 2: A Practical Approach*. Oxford University Press, 1995; Higgins and Hames, eds. *Protein Expression: A Practical Approach*. Oxford University Press, 1999); Freshney, ed. *Animal Cell Culture*. 1986; Masters, ed. *Animal Cell Culture: A Practical Approach*. Oxford University Press, 2000; Davis, ed *Basic Cell Culture $2^{nd}$ Edition*. Oxford University Press, 2002; *High Resolution Chromatography: A Practical Approach*. Oxford University Press, 1999; Oliver, ed. *HPLC of Macromolecules: A Practical Approach*. Oxford University Press, 1998; Matejtschuk, ed, *Immunoassays: A Practical Approach*. Oxford University Press, 2000; Hames, ed. *Gel Electrophoresis of Proteins: A Practical Approach*. Oxford University Press, 1998; Harlow and Lane. *Using Antibodies: A Laboratory Manual*. Cold Spring Harbor Laboratory Press, 1999; Coligan et al., eds. *Current Protocols in Immunology, Vol. 1*. Wiley & Sons, 2000; Hockfield et al. *Selected Methods for Antibody and Nucleic Acid Probes*. Cold Spring Harbor Laboratory Press, 1993; and Higgins and Hames, eds. *Post-Translational Processing: A Practical Approach*. Oxford University Press, 1999).

For example, the protein may be expressed in a mammalian cell, such as a human ovarian cell line, extracellular fluid collected, and the presence or absence of the protein in the extracellular fluid assessed via an immunoassay using a labeled antibody which binds specifically to the protein.

In the context of the present invention, it is further preferable that the protein associated with a genotype be expressed in the embryo. For example, the protein may be a protein that is ubiquitously expressed (i.e., expressed in all cell types at all times). In another example, the protein may be a protein that is expressed in a tissue-specific and/or stage specific manner, where the protein is expressed in at least one cell type of the embryo at the stage examined. For example, in embodiments where the embryo is a preimplantation embryo having from 6 to 8 cells, it is preferable that the protein be expressed in at least one blastomere of the 6 to 8 cell embryo.

It is within the skill of one of ordinary skill in the art to determine the expression pattern of a protein in an embryo of a given developments stage. For example, the expression of an mRNA encoding the protein may be assessed, for example by Northern blotting, RT-PCR, or in situ hybridization. For example, the expression of the protein may be assessed, for example, by immunohistochemistry. Such techniques are well established in the art (see, for example, (see, for example, Glover, ed. *DNA Cloning: A Practical Approach. $2^{nd}$ Edition. Volumes I-IV*. Oxford University Press, 1999; Ausubel et al., eds. *Current Protocols in Molecular Biology*. John Wiley & Sons, Inc., 1994; Dieffenbach and Dveksler, eds. *PCR Primer: A Laboratory Manual. $2^{nd}$ Edition*. Cold Spring Harbor Laboratory Press, 2003; Sambrook et al. *Molecular Cloning: A Laboratory Manual, Third Edition*. Cold Spring Harbor Laboratory Press, 2001; McPherson et al., eds. *PCR: A Practical Approach*. Oxford University Press, 1991; McPherson et al., eds. *PCR 2: A Practical Approach*. Oxford University Press, 1995; Herrington and O'Leary, eds. *PCR 3: PCR In Situ Hybridization*. Oxford University Press, 1998; Higgins and Hames, eds. *Protein Expression: A Practical Approach*. Oxford University Press, 1999); Freshney, ed. *Animal Cell Culture*. 1986; Masters, ed. *Animal Cell Culture: A Practical Approach*. Oxford University Press, 2000; Davis, ed *Basic Cell Culture $2^{nd}$ Edition*. Oxford University Press, 2002; *High Resolution Chromatography: A Practical Approach*. Oxford University Press, 1999; Oliver, ed. *HPLC of Macromolecules: A Practical Approach*. Oxford University Press, 1998; Matejtschuk, ed, *Immunoassays: A Practical Approach*. Oxford University Press, 2000; Hames, ed. *Gel Electrophoresis of Proteins: A Practical Approach*. Oxford University Press, 1998; Harlow and Lane. *Using Antibodies: A Laboratory Manual*. Cold Spring Harbor Laboratory Press, 1999; Coligan et al., eds. *Current Protocols in Immunology, Vol. 1*. Wiley & Sons, 2000; and Hockfield et al. *Selected Methods for Antibody and Nucleic Acid Probes*. Cold Spring Harbor Laboratory Press, 1993).

In particular embodiments, the genotype is the presence or absence of the Y chromosome and the protein associated with the genotype is a protein associated with the Y chromosome.

Protein Associated with the Y Chromosome

By the term "protein associated with the Y chromosome" is meant any protein whose presence is specifically correlated with the presence of the Y chromosome. Proteins associated with the Y chromosome include proteins whose coding sequences are contained on the Y chromosome, such that in the absence of the Y chromosome, the proteins are not expressed. Proteins associated with the Y chromosome also include proteins whose coding sequences are contained on a chromosome other than Y chromosome, but which are not expressed in the absence of the Y chromosome.

Proteins whose coding sequences are contained on the Y chromosome include those set forth in Table 1.

TABLE 1

Proteins unique to the Y Chromosome.

| Gene symbol | Gene name | Protein | Copies |
|---|---|---|---|
| *X Transposed region* | | | |
| TGIF2LY | TGFβ-induced factor 2-like, Y linked | TGFβ-induced transcription factor 2-like protein | 1 |
| PCDH11Y | Protocadherin 11 Y | Protocadherin | 1 |
| *X degenerate* | | | |
| SRY | Sex determining region | Sex determining region Y protein | 1 |
| RPS4Y1 | Ribosomal protein S4 Y isoform 1 | Ribosomal protein S4 Y isoform 1 | 1 |
| ZFY | Zinc finger Y | Zinc finger Y chromosomal protein | 1 |
| AMELY | Amelogenin Y | Amelogenin Y | 1 |
| TBL1Y | Transducin (beta) like 1 protein Y | Transducin (beta) like 1 protein Y | 1 |
| PRKY | Protein kinase Y | Protein kinase Y | 1 |
| USP9Y | Ubiquitin specific protease 9Y | Ubiquitin specific protease 9Y | 1 |
| DBY | Dead Box Y | Dead Box Y protein | 1 |
| UTY | Ubiquitous TPR motif Y | Ubiquitous TPR motif Y | 1 |
| TMSB4Y | Thymosin (beta) 4 Y | Thymosin (beta) 4 Y | 1 |
| NLGN4Y | Neuroligin 4 isoform Y | Neuroligin 4 isoform Y | 1 |
| Cyorf15A | Chromosome Y open reading frame 15A | Chromosome Y open reading frame 15A | 1 |
| SMCY | SMC (mouse) homolog, Y | SMC (mouse) homolog | 1 |
| EIF1AY | Translation initiation factor 1AY | Translation initiation factor 1AY | 1 |
| RPS4Y2 | Ribosomal protein S4 Y isoform 2 | Ribosomal protein S4 Y isoform 2 | 1 |
| *Amplionic* | | | |
| TSPY | Testis specific protein Y | Testis specific protein Y | 6 |
| VCY | Variable charge Y | Variable charge Y | 2 |
| XKRY | XK related Y | XK related Y protein | 2 |
| CDY | Chromodomain Y | Chromodomain protein | 4 |
| HSFY | Heat shock transcription factor Y | Heat shock transcription factor protein Y | 2 |
| RBMY | RNA binding motif Y | RNA binding motif Y protein | 6 |
| PRY | PTP-BL related Y | PTP-BL related Y protein | 2 |
| DAZ | Deleted in azoospermia | DAZ | 4 |

Thus, in particular embodiments, the protein associated with the Y chromosome is selected from the group consisting of: TGFβ-induced transcription factor 2-like protein, Protocadherin 11Y, Sex determining region Y protein, Ribosomal protein S4 Y isoform 1, Zinc finger Y chromosomal protein, Amelogenin Y, Transducin (beta) like 1 protein Y, Protein kinase Y, Ubiquitin specific protease 9Y, Dead Box Y protein, Ubiquitous TPR motif Y, Thymosin (beta) 4 Y, Neuroligin 4 isoform Y, Chromosome Y open reading frame 15A, Chromosome Y open reading frame 15B, SMC (mouse) homolog, Translation initiation factor 1AY, Ribosomal protein S4 Y isoform 2, Testis specific protein Y, Variable charge Y, XK related Y protein, Chromodomain Y protein, Heat shock transcription factor protein Y, RNA binding motif Y protein, PTP-BL related Y protein, Deleted in azoospermia (DAZ), novel protein similar to lysozyme C, and mixtures thereof.

In other embodiments, the protein associated with the Y chromosome is a Homo sapiens similar to RNA binding motif protein, Y chromosome, family 2 member B (LOC347598) protein. Exemplary nucleotide and amino acid sequences for this protein are set forth as SEQ ID NO: 1 and SEQ ID NO: 2, respectively.

The invention also provides a method for identifying a protein associated with the Y chromosome, which comprises: (a) detecting the presence of at least one protein in a sample of culture medium obtained by sampling a culture medium containing a male embryo; (b) detecting the presence of at least one protein in a sample of culture medium obtained by sampling a culture medium containing a female embryo; and (c) identifying a protein associated with the Y chromosome as a protein present in the sample of culture medium of step (a) but absent in the sample of culture medium of step (b). It is within the skill of one of ordinary skill in the art to provide (e.g., by PGD of an IVF generate embryo or sex selection of sperm prior to IVF) a male embryo to be used in the context of this method of the invention.

Thus, in the method for identifying a sex of an embryo, the protein associated with the Y chromosome may be a protein associated with the Y chromosome as identified according to the method for identifying a protein associated with the Y chromosome.

Sampling a Culture Medium Containing an Embryo

Techniques for in vitro culture of mammalian cells are well established in the art (see, for example, Freshney, ed. *Animal Cell Culture*. 1986; Masters, ed. *Animal Cell Culture: A Practical Approach*. Oxford University Press, 2000; Davis, ed *Basic Cell Culture* 2$^{nd}$ *Edition*. Oxford University Press, 2002), including techniques for the in vitro culture of mammalian embryos, including pre-implantation embryos (see, for example Cohen et al. *Br Med Bull* 1990; 46:643-653; Wilmut et al. *Nature* 1997; 385:810-813; Cibelli et al. *Science* 1998; 280:1256-8; Keefer et al. *Biology of Reproduction* 2001; 64:849-856; Hogan et al. *Manipulating the Mouse Embryo* 2$^{nd}$ *Edition*. Cold Spring Harbor Press, 1994; Jackson and Abbott, eds. *Mouse Genetics and Transgenics: A Practical Approach*. Oxford University Press, 2000; U.S. Pat. No. 5,633,076; U.S. Pat. No. 6,271,436; U.S. Pat. No. 5,907,080; and U.S. Pat. No. 6,147,276;). For example, techniques for the in vitro culture of embryos are well established for mice (see, for example, Hogan et al. *Manipulating the Mouse Embryo 2nd Edition*. Cold Spring Harbor Press, 1994), rabbits (see, for example, Hammer et al. *Nature* 1985; 315:680) sheep (see, for example, Hammer et al. *Nature* 1985; 315:680; Gandolfi et al. *J. Reprod. Fert.* 1987; 81:23-28; and Rexroad et al. *J. Anim. Sci.* 1988; 66:947-953), pigs (see, for example, Hammer et al. *Nature* 1985; 315:680); cows (see, for example, Eyestone et al. *J. Reprod. Fert* 1989; 85:715-720 and Goto. Mol Reprod Devel. 1993; 36:288-290), and humans (see, for example, Boiso et al. *Reprod Biomed Online.* 2002; 5:328-350; Devreker and Englert. Eur J Obstet Gynecol Reprod Biol 2000; 92:51-56; and Gardner and Lane. Hum Reprod. 1998; 13:148-159).

Thus, the culture medium containing an embryo may be any culture medium known in the art and used for the culture of mammalian cells and/or embryos. The culture medium containing the embryo may be conveniently sampled using any of the methods well known in the art, including aspiration, decanting, and pipetting.

Detecting a Protein Associated with a Genotype in a Sample of Culture Medium

The presence of a protein associated with a genotype may be detected in the culture medium sample by any of the means well established in the art, including chromatography [such as High Pressure Liquid Chromatography (HPLC)], affinity separation, Such techniques are well described in the art (see, for example, Millner, ed. *High Resolution Chromatography: A Practical Approach*. Oxford University Press, 1999; Oliver, ed. *HPLC of Macromolecules: A Practical Approach*. Oxford University Press, 1998; Matejtschuk, ed, *Affinity Separations: A Practical Approach*. Oxford University Press, 1997; Gosling, ed. *Immunoassays: A Practical Approach*. Oxford University Press, 2000; Johnstone and Turner, eds. *Immunochemistry 1 and 2: A Practical Approach*. Oxford University Press, 1997; McCafferty et al., eds. *Antibody Engineering: A Practical Approach*. Oxford University Press, 1996; Shepherd and Dean, eds. *Monoclonal Antibodies: A Practical Approach*. Oxford University Press, 2000; Coligan et al., eds. *Current Protocols in Immunology, Vol.* 1. Wiley & Sons, 2000; Harlow and Lane. *Using Antibodies: A Laboratory Manual*. Cold Spring Harbor Laboratory Press, 1999; Hockfield et al. *Selected Methods for Antibody and Nucleic Acid Probes*. Cold Spring Harbor Laboratory Press, 1993; Hames, ed. *Gel Electrophoresis of Proteins: A Practical Approach*. Oxford University Press, 1998; and Gore, ed. *Spectrophotometry and Spectrofluorimetry: A Practical Approach*. Oxford University Press, 2000.

In particular embodiments, the presence of protein associated with a genotype may be detected in the culture medium using an immunoassay, such as the enzyme linked immunosorbent assay, using one or more antibodies directed against the protein. Such antibodies may be generated by any of the techniques well described in the art (see, for example, *Immunoassays: A Practical Approach*. Oxford University Press, 2000; Johnstone and Turner, eds. *Immunochemistry 1 and 2: A Practical Approach*. Oxford University Press, 1997; McCafferty et al., eds. *Antibody Engineering: A Practical Approach*. Oxford University Press, 1996; Shepherd and Dean, eds. *Monoclonal Antibodies: A Practical Approach*. Oxford University Press, 2000; Coligan et al., eds. *Current Protocols in Immunology, Vol.* 1. Wiley & Sons, 2000; Harlow and Lane. *Using Antibodies: A Laboratory Manual*. Cold Spring Harbor Laboratory Press, 1999; Hockfield et al. *Selected Methods for Antibody and Nucleic Acid Probes*. Cold Spring Harbor Laboratory Press, 1993.)

For example, the presence of the protein may be detected assessed using an labeled antibody (e.g. a radiolabeled, chromophore-labeled, fluorophore-labeled, or enzyme-labeled antibody), an antibody conjugate (e.g. an antibody conjugated with a substrate or with the protein or ligand of a protein-ligand pair, e.g. biotin-streptavidin), or an antibody fragment (e.g. a single-chain antibody, an isolated antibody hypervariable domain, etc.) or derivative which binds specifically with the protein or fragment thereof, including a protein which has undergone all or a portion of its normal post-translational modification. Examples of suitable enzymes for antibody labeling include horseradish peroxidase, alkaline phosphatase, beta-galactosidase, or acetylcholinesterase. Examples of suitable fluorophores include umbelliferone, fluorescein, fluorescein isothiocyanate, rhodamine, dichloro-triazinylamine fluorescein, dansyl chloride or phycoerythrin.

In another embodiment, the presence of the protein may be detected via fluorescence energy transfer (see, for example, U.S. Pat. No. 5,631,169 and U.S. Pat. No. 4,868,103).

OTHER EMBODIMENTS OF THE METHOD OF THE INVENTION

In other embodiments of the invention, the present method may also be applied to determine a genotype of an embryo where the genotype is associated with a lower or higher level of expression of a particular protein, rather than strict presence or absence of the protein. In this case, the genotype of an embryo is determined by sampling a culture medium containing the embryo and detecting the level of a protein associated with the genotype in the culture medium sample, and comparing the level of the protein associated with the genotype detected in the culture medium sample with a level of said protein detected in a culture medium sample of a control embryo of known genotype (e.g., as determined by PGD), wherein if the detected levels of said protein are roughly equivalent, then the genotype of the embryo is identified as the same as that of the control embryo.

In still other embodiments, the invention provides a method to diagnose a genetic disease or condition in an embryo by sampling a culture medium containing the embryo and detecting the presence of a protein associated with the genetic disease or condition in the culture medium sample, wherein the presence or absence of the protein associated with the genetic disease or condition serves to diagnose the genetic disease or condition in the embryo.

Similarly, the invention further provides a method to diagnose a genetic disease or condition in an embryo where the genetic disease or condition is associated with a lower or higher level of expression of a particular protein, rather than strict presence or absence of the protein. In this case, the a genetic disease or condition is diagnosed in an embryo by sampling a culture medium containing the embryo and detecting the level of a protein associated with the genetic disease or condition in the culture medium sample, and comparing the level of the protein associated with the genetic disease or condition detected in the culture medium sample with a level of said protein detected in a culture medium sample of a control embryo having said genetic disease or condition (e.g., as determined by PGD), wherein if the detected levels of said protein are roughly equivalent, then the embryo is diagnosed as having the genetic disease of condition.

The present invention also provides methods to identify a protein associated with a genetic disease or condition by: (a) sampling culture medium containing an embryo which does not have the genetic disease or condition (e.g., as determined by PGD) and detecting the level of at least one protein in the sampled culture medium and (b) sampling culture medium containing an embryo which does not have the genetic disease or condition (e.g., as determined by PGD) and detecting the level of at least one protein in the sampled culture medium, wherein a protein detected in (a) but not in (b) is identified as a protein associated with the genetic disease or condition or wherein a protein detected in (b) but not in (a) is identified as a protein associated with the genetic disease or condition.

EXAMPLES

The present invention is next described by means of the following examples. However, the use of these and other examples anywhere in the specification is illustrative only, and in no way limits the scope and meaning of the invention or of any exemplified form. Likewise, the invention is not limited to any particular embodiments described herein. Indeed, many modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Example 1

Embryo Sex Determination by Detection of Y Chromosome Associated Protein in Samples of Culture Media from IVF-Generated Embryos Human embryos are generated by in vitro fertilization (IVF) according to standard protocols. The IVF-generated embryos are each placed in individual vials containing culture medium. On Day 3, 35 µl of exposed media is removed from each vial. As control, an equal amount (35 µl) of media is sampled from drops that did not contain an embryo. The media collection procedure is repeated on Day 5 (day when embryo transfer into recipient female is normally performed). All samples are collected using sterile pipette tips and a 20-200 µl pipetter. All sampled media is snap frozen in NAL-GENE cryo vials by plunging the sampled media into liquid nitrogen. Samples can be analyzed on-site or transported to another facility using a standard liquid nitrogen transport tank. The culture medium samples are analyzed for the presence or absence of a Y chromosome associated protein. Embryos whose samples contain the Y chromosome associated protein are identified as male, while embryos whose samples do not contain the Y chromosome associated protein are identified as female.

Embryo biopsy for preimplantation genetic diagnosis (PGD) is also performed on days 3 and 5. PGD is performed to determine the presence or absence of the Y chromosome in each biopsied blastomere according to standard protocols. Embryos whose blastomeres contain the Y chromosome are identified as male, while embryos whose blastomeres do not contain the Y chromosome are identified as female.

Results from each individual embryo PGD biopsy regarding presence or absence of the Y chromosome is compared with the results for each individual embryo for the presence or absence of the Y chromosome associated protein in the culture medium samples. Comparisons are made for both Day 3 and Day 5 data. The results confirm that presence or absence of the Y chromosome associated protein in culture medium sample for a given embryo correlates with presence or absence of the Y chromosome in biopsied blastomeres for the same embryo, confirming that the sex of the embryo is accurately identified by the presence or absence of the Y chromosome associated protein in culture medium.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method to determine a genotype of an embryo, which comprises:
   (a) sampling a culture medium containing an embryo; and
   (b) detecting the presence of a protein associated with the genotype in the sample of culture medium,
   wherein the presence or absence of the protein associated with the genotype determines the genotype of the embryo;
   wherein the sampled medium does not include the embryo.

2. The method of claim 1, wherein the embryo is a human embryo.

3. The method of claim 1, wherein the embryo has a total cell number of from 6 to 8 cells.

4. A method for identifying the sex of an embryo, which comprises:
   (a) sampling a culture medium containing an embryo;
   (b) detecting the presence of a protein associated with the Y chromosome in the sample of culture medium; and
   (c) identifying the sex of the embryo as a male if a protein associated with the Y chromosome in present or as a female if a protein associated with the Y chromosome is not present;
   wherein the sampled medium does not include the embryo.

5. The method of claim 4, wherein the protein associated with the Y chromosome is selected from the group consisting of: TGFβ-induced transcription factor 2-like protein, Protocadherin 11Y, Sex determining region Y protein, Ribosomal protein S4 Y isoform 1, Zinc finger Y chromosomal protein, Amelogenin Y, Transducin (beta) like 1 protein Y, Protein kinase Y, Ubiquitin specific protease 9Y, Dead Box Y protein, Ubiquitous TPR motif Y, Thymosin (beta) 4 Y, Neuroligin 4 isoform Y, Chromosome Y open reading frame 15A, Chromosome Y open reading frame 15B, SMC (mouse) homolog, Translation initiation factor 1AY, Ribosomal protein S4 Y isoform 2, Testis specific protein Y, Variable charge Y, XK related Y protein, Chromodomain Y protein, Heat shock transcription factor protein Y, RNA binding motif Y protein, PTP-BL related Y protein, Deleted in azoospermia (DAZ), novel protein similar to lysozyme C, and mixtures thereof.

6. The method of claim 4, wherein the protein associated with the Y chromosome is a Homo sapiens similar to RNA binding motif protein, Y chromosome, family 2 member B (LOC347598) protein.

7. The method of claim 4, wherein the embryo is a human embryo.

8. The method of claim 4, wherein the embryo has a total cell number of from 6 to 8 cells.

9. A method for identifying a protein associated with the Y chromosome, which comprises:
  (a) detecting the presence of at least one protein in a sample of culture medium obtained by sampling a culture medium containing a male embryo;
  (b) detecting the presence of at least one protein in a sample of culture medium obtained by sampling a culture medium containing a female embryo; and
  (c) identifying a protein associated with the Y chromosome as a protein present in the sample of culture medium of step (a) but absent in the sample of culture medium of step (b);
  wherein the sampled media do not include the embryo.

10. The method of claim 9, wherein the male embryo and the female embryo are both human embryos.

11. The method of claim 9, wherein the male embryo has a total cell number of from 6 to 8 cells and the female embryo has a total cell number of from 6 to 8 cells.

12. A method for identifying the sex of an embryo, which comprises:
  (a) sampling a culture medium containing an embryo;
  (b) detecting the presence of a protein associated with the Y chromosome in the sample of culture medium; and
  (c) identifying the sex of the embryo as a male if a protein associated with the Y chromosome in present or as a female if a protein associated with the Y chromosome is not present, wherein the protein associated with the Y chromosome is identified according to the method of claim 9.

13. The method of claim 12, wherein the embryo is a human embryo.

14. The method of claim 12, wherein the embryo has a total cell number of from 6 to 8 cells.

* * * * *

SEQUENCE LISTING

```
<160> NUMBER OF SEQ ID NOS: 2

<210> SEQ ID NO 1
<211> LENGTH: 3123
<212> TYPE: DNA
<213> ORGANISM: Homo sapiens

<400> SEQUENCE: 1
atgcctggat ctcagtctgg acccaagcct gaacaacaac ctcttaggta ttcagaactc      60
agtgtttccc tggaaagtcc tggaattgtg caaaaacggc acctgagcat cctacaagtc     120
agcacttgtg cccaattttg gctcaagctg aatgaactca ctttctgggt ggaggccaag     180
aaagccatgt ggatggctga ctatcaggga gtgacacagt ctagctatgc tccctggtac     240
aagcaagggc ccatgactac ctctgcttct atgtcccatt cagtctctac ctctacaaat     300
gcttcagctt ttacctccac ccctgcttct ctttggccac acttctctct gccacagcct     360
cagagtaagg ctcaaaaact tggtagagat cagatttatc tgcgatatgc catgccttgg     420
```

-continued

```
aaggctgtca tcatcatctg tgggagtcag atctgcagtg gttccatagt tggcagctct      480
tggattctca cagctgccca ctgtgtcagg aacatggatc tgaagacac tgctgtgata       540 ctgggcctga ggcaccctga ggcaccactg agagttgtga aggtgtctac cattctactg      600
catgacagat tctggttggt gactgaggca gcaagaaata ttctggaatt gctactcctc      660
cacgatgtcc agactcccat ttggctctta tcactcttgg gctatctgag gaacctgaat      720
agttcagaat gctggctctc taggccacat attgttacac cagctgtcct gcttagacac      780
ccctgggccc caggggggacc gcaacctcac ccaggcactg gaccactccc acagattcag     840
gctcagcagc ctaacctgca aatccatcat gtagctcagc aggacttcat catttgtgac      900
cctggtccat atctgggccc aagtcttgag caccatgtgt ttctggggcc gccctctccc      960
gcagagcctc cagacttaac acggtgccct cctaggctc ccacagacca agggctcaca      1020
gtctgcgtgt gcctgaaccc accaccacct tgcacaagca tcttctcaga ggaggactac      1080
cgcgggagga tggagctgca ggccacccag ggggagggct cctcaggaga cgcctaccgc      1140
tcttgcaata attggcagat gcccactgcc ttcccaatga ttggctggag cacaatggta      1200
gaagcagatt gtcatggcaa gcttttcatt ggtggcctca atagagaagc caatgaaaag      1260
gtgcttaaag aagtatttgc aaaacatggt ccccttttgg aagttctttt gataaaaggt      1320
cgaaccagta agtccagaga ttttgtggtc attattttg agaatgctgc agatgctaag       1380
aatgctgcca gagatatgaa tggaaagtct ttggatggaa aagaaataaa agtagaacaa      1440
gcaaagaaac catctttttcc aagtggtggt aggcggagac caccaccttc ttcaagaaac     1500
agaagccctt caggaagtct gagatctgca agaggaagta gtggaggaac aagaccgtgg      1560 ctgcccctcac atgaaggaca cttggatgat ggtggatacg ctcttgatct caacacgagt     1620
tcttctaggg gagccattcc aattaaaaga ggtccatctt cacgaagtgg aggtcctcct      1680
cctaaaacat ctgctccttc tgctatggca agaagcaata gttggatggg aggccaaggt      1740
cccatatcac gtggaagaga gaattatgga ggtcctccat gcagagagcc aatctcttcc      1800
tggagaaatg accgtatgtc accaagagat gatggttatg caattaagga agaaatcat     1860 ccactttccc gagaatctag ggattatgct ccactgtcta gagactatgc ataccatgat      1920
tatggtcatt ctagttggga tgaacatttc tctagaggat ataggtatta caacatttcc      1980
tggacttgtc aaatagaatt cttaaatgct ctttcccttc ccattatcct gctgctggga      2040
aagatggcag gaccctggaa tggagaaggg ccctgggttg ttgacagtgc ctgtgggtgg      2100
tcatgtacta ggaggagagt cctcactgag cctcctgtga gcttggaggc tgggaaggaa      2160
cacttatggg gcactggctg ttccagagtc caggggcctg tcccggagaa gcctgggggg      2220
aagtcgttaa gcctgtggtt ctgcaatcta ggtggaagag ctgtatctgc catggctgac      2280
atcatcaggg caagacaccc actgggtgga gagctggact tatgcatttt tatccctgtc      2340
ctgaagggac cctgcatgcc tgcctctccg ggaccagtc atcctgggga cccctctct       2400 gggaccactc atgaccataa gcttaggctc ttgtgtgcct tgcttcctgt ctgcccagtg      2460
gtcacggtca gccaaccagc ggaagaagct cagttaggct gtgtcctgcc tgaagctggg      2520
gtcttctgct gcatgactct agaaacactg gactacagta gagacagatg ccatgtatcc      2580
tggagcaaga agatttggga cttcctcatg gtttctgaaa cctgccgaca tctgggtgtg      2640
cggcacaatc tgcctctggt caaggagcct ccagatgact gggtcaccct caagcaagct      2700
gccctactat ctgcagtatc cttgcctcag ctcccctcgc tgtctcccat cccctgcctc      2760
ctggctgacc ctgtgtgccc ctggcctggc tccgttgctc cccgccccccg gaagcccgac    2820
```

-continued

```
tcccacctcc tgctgccagt catcccgaat gggcagttac aaagatatgg ctctggccta    2880
gaagccggag atgccctgga tgatggcccc tgtgccctcc aggccaggca gacacttctg    2940
acaaagcttc tgcctcagcc atgggcaggg catgtggcct ggggcattca cggagcccag    3000
ctccctgtga aggacctcca gcgactctgt ggccggctgg ggcatgctgg ggccagggca    3060
ggctgtgttc actggtcctc cacctgccgc tccatgtcgg ctttctcctc aaccaccacc    3120
tag                                                                  3123
```

<210> SEQ ID NO 2
<211> LENGTH: 1040
<212> TYPE: PRT
<213> ORGANISM: Homo sapiens

<400> SEQUENCE: 2

```
Met Pro Gly Ser Gln Ser Gly Pro Lys Pro Glu Gln Gln Pro Leu Arg
1               5                   10                  15

Tyr Ser Glu Leu Ser Val Ser Leu Glu Ser Pro Gly Ile Val Gln Lys
            20                  25                  30

Arg His Leu Ser Ile Leu Gln Val Ser Thr Cys Ala Gln Phe Trp Leu
35                  40                  45

Lys Leu Asn Glu Leu Thr Phe Trp Val Glu Ala Lys Lys Ala Met Trp
50                  55                  60

Met Ala Asp Tyr Gln Gly Val Thr Gln Ser Ser Tyr Ala Pro Trp Tyr
65                  70                  75                  80

Lys Gln Gly Pro Met Thr Thr Ser Ala Ser Met Ser His Ser Val Ser
            85                  90                  95

Thr Ser Thr Asn Ala Ser Ala Phe Thr Ser Thr Pro Ala Ser Leu Trp
100                 105                 110

Pro His Phe Ser Leu Pro Gln Pro Gln Ser Lys Ala Gln Lys Leu Gly
115                 120                 125

Arg Asp Gln Ile Tyr Leu Arg Tyr Ala Met Pro Trp Lys Ala Val Ile
130                 135                 140

Ile Ile Cys Gly Ser Gln Ile Cys Ser Gly Ser Ile Val Gly Ser Ser
145                 150                 155                 160

Trp Ile Leu Thr Ala Ala His Cys Val Arg Asn Met Asp Pro Glu Asp
            165                 170                 175

Thr Ala Val Ile Leu Gly Leu Arg His Pro Glu Ala Pro Leu Arg Val
180                 185                 190

Val Lys Val Ser Thr Ile Leu Leu His Asp Arg Phe Trp Leu Val Thr
195                 200                 205

Glu Ala Ala Arg Asn Ile Leu Glu Leu Leu Leu His Asp Val Gln
210                 215                 220

Thr Pro Ile Trp Leu Leu Ser Leu Leu Gly Tyr Leu Arg Asn Leu Asn
225                 230                 235                 240

Ser Ser Glu Cys Trp Leu Ser Arg Pro His Ile Val Thr Pro Ala Val
            245                 250                 255

Leu Leu Arg His Pro Trp Ala Pro Gly Gly Pro Gln Pro His Pro Gly
260                 265                 270

Thr Gly Pro Leu Pro Gln Ile Gln Ala Gln Pro Asn Leu Gln Ile
275                 280                 285

His His Val Ala Gln Gln Asp Phe Ile Ile Cys Asp Pro Gly Pro Tyr
290                 295                 300

Leu Gly Pro Ser Leu Glu His His Val Phe Leu Gly Pro Pro Ser Pro
```

-continued

```
            305                 310                 315                 320
Ala Glu Pro Pro Asp Leu Thr Arg Cys Pro Pro Arg Ala Pro Thr Asp
325                 330                 335
Gln Gly Leu Thr Val Cys Val Cys Leu Asn Pro Pro Pro Cys Thr
340                 345                 350
Ser Ile Phe Ser Glu Glu Asp Tyr Arg Gly Arg Met Glu Leu Gln Ala
355                 360                 365
Thr Gln Gly Arg Gly Ser Ser Gly Asp Ala Tyr Arg Ser Cys Asn Asn
370                 375                 380
Trp Gln Met Pro Thr Ala Phe Pro Met Ile Gly Trp Ser Thr Met Val
385                 390                 395                 400
Glu Ala Asp Cys His Gly Lys Leu Phe Ile Gly Gly Leu Asn Arg Glu
405                 410                 415
Ala Asn Glu Lys Val Leu Lys Glu Val Phe Ala Lys His Gly Pro Leu
420                 425                 430
Leu Glu Val Leu Leu Ile Lys Gly Arg Thr Ser Lys Ser Arg Asp Phe
435                 440                 445
Val Val Ile Ile Phe Glu Asn Ala Ala Asp Ala Lys Asn Ala Ala Arg
450                 455                 460
Asp Met Asn Gly Lys Ser Leu Asp Gly Lys Glu Ile Lys Val Glu Gln
465                 470                 475                 480
Ala Lys Lys Pro Ser Phe Pro Ser Gly Gly Arg Arg Pro Pro Pro
485                 490                 495
Ser Ser Arg Asn Arg Ser Pro Ser Gly Ser Leu Arg Ser Ala Arg Gly
500                 505                 510
Ser Ser Gly Gly Thr Arg Pro Trp Leu Pro Ser His Glu Gly His Leu
515                 520                 525
Asp Asp Gly Gly Tyr Ala Leu Asp Leu Asn Thr Ser Ser Ser Arg Gly
530                 535                 540
Ala Ile Pro Ile Lys Arg Gly Pro Ser Ser Arg Ser Gly Gly Pro Pro
545                 550                 555                 560
Pro Lys Thr Ser Ala Pro Ser Ala Met Ala Arg Ser Asn Ser Trp Met
565                 570                 575
Gly Gly Gln Gly Pro Ile Ser Arg Gly Arg Glu Asn Tyr Gly Gly Pro
580                 585                 590
Pro Cys Arg Glu Pro Ile Ser Ser Trp Arg Asn Asp Arg Met Ser Pro
595                 600                 605
Arg Asp Asp Gly Tyr Ala Ile Lys Glu Arg Asn His Pro Leu Ser Arg
610                 615                 620
Glu Ser Arg Asp Tyr Ala Pro Leu Ser Arg Asp Tyr Ala Tyr His Asp
625                 630                 635                 640
Tyr Gly His Ser Ser Trp Asp Glu His Phe Ser Arg Gly Tyr Arg Tyr
645                 650                 655
Tyr Asn Ile Ser Trp Thr Cys Gln Ile Glu Phe Leu Asn Ala Leu Ser
660                 665                 670
Leu Pro Ile Ile Leu Leu Gly Lys Met Ala Gly Pro Trp Asn Gly
675                 680                 685
Glu Gly Pro Trp Val Val Asp Ser Ala Cys Gly Trp Ser Cys Thr Arg
690                 695                 700
Arg Arg Val Leu Thr Glu Pro Pro Val Ser Leu Glu Ala Gly Lys Glu
705                 710                 715                 720
His Leu Trp Gly Thr Gly Cys Ser Arg Val Gln Gly Pro Val Pro Glu
725                 730                 735
```

-continued

```
Lys Pro Gly Gly Lys Ser Leu Ser Leu Trp Phe Cys Asn Leu Gly Gly
740                 745                 750
Arg Ala Val Ser Ala Met Ala Asp Ile Ile Arg Ala Arg His Pro Leu
755                 760                 765
Gly Gly Glu Leu Asp Leu Cys Ile Phe Ile Pro Val Leu Lys Gly Pro
770                 775                 780
Cys Met Pro Ala Ser Pro Gly Thr Ser His Pro Gly Asp Pro Leu Ser
785                 790                 795                 800
Gly Thr Thr His Asp His Lys Leu Arg Leu Leu Cys Ala Leu Leu Pro
805                 810                 815
Val Cys Pro Val Val Thr Val Ser Gln Pro Ala Glu Glu Ala Gln Leu
820                 825                 830
Gly Cys Val Leu Pro Glu Ala Gly Val Phe Cys Cys Met Thr Leu Glu
835                 840                 845
Thr Leu Asp Tyr Ser Arg Asp Arg Cys His Val Ser Trp Ser Lys Lys
850                 855                 860
Ile Trp Asp Phe Leu Met Val Ser Glu Thr Cys Arg His Leu Gly Val
865                 870                 875                 880
Arg His Asn Leu Pro Leu Val Lys Glu Pro Pro Asp Asp Trp Val Thr
885                 890                 895
Leu Lys Gln Ala Ala Leu Leu Ser Ala Val Ser Leu Pro Gln Leu Pro
900                 905                 910
Ser Leu Ser Pro Ile Pro Cys Leu Leu Ala Asp Pro Val Cys Pro Trp
915                 920                 925
Pro Gly Ser Val Ala Pro Arg Pro Arg Lys Pro Asp Ser His Leu Leu
930                 935                 940
Leu Pro Val Ile Pro Asn Gly Gln Leu Gln Arg Tyr Gly Ser Gly Leu
945                 950                 955                 960
Glu Ala Gly Asp Ala Leu Asp Asp Gly Pro Cys Ala Leu Gln Ala Arg
965                 970                 975
Gln Thr Leu Leu Thr Lys Leu Leu Pro Gln Pro Trp Ala Gly His Val
980                 985                 990
Ala Trp Gly Ile His Gly Ala Gln  Leu Pro Val Lys Asp  Leu Gln Arg
995                 1000                1005
Leu Cys  Gly Arg Leu Gly His  Ala Gly Ala Arg Ala  Gly Cys Val
1010                 1015                1020
His Trp  Ser Ser Thr Cys Arg  Ser Met Ser Ala Phe  Ser Ser Thr
1025                 1030                1035
Thr Thr
1040
```